United States Patent [19]

Smith et al.

[11] Patent Number: 4,747,967

[45] Date of Patent: May 31, 1988

[54] USE OF AMINE OXIDE IN THE $H_2O_2$ OXIDATION OF ALIPHATIC MERCAPTAN TO SULFONIC ACID

[75] Inventors: Kim R. Smith; Joe D. Sauer; James E. Borland, all of Baton Rouge, La.

[73] Assignee: Ethyl Corporation, Richmond, Va.

[21] Appl. No.: 737,559

[22] Filed: May 24, 1985

[51] Int. Cl.$^4$ .................................. C07C 143/02
[52] U.S. Cl. .................................. 260/513 R
[58] Field of Search .................................. 260/513 R

[56] References Cited

U.S. PATENT DOCUMENTS 2,727,920 12/1955 Johnson et al. ............... 260/513 R
4,239,696 12/1980 Schreyer et al. ............. 260/513 R

OTHER PUBLICATIONS

Chem. Abst. vol. 65 (1966), 16923 Oda et al.
Oswald J. Org. Chem., vol. 28 (1963), 651–657.
Hayaski Japan Kokai No. 52-111486, Sep. 1977 (Abstract).

*Primary Examiner*—Alan Siegel
*Attorney, Agent, or Firm*—J. F. Sieberth; J. D. Odenweller

[57] ABSTRACT

Hydrocarbyl mercaptans are oxidized to sulfonic acids by reaction with aqueous hydrogen peroxide in the presence of an inorganic base (e.g. sodium hydroxide) and a tert-amine oxide. The product is in the form of a sulfonate salt. The reaction rate is increased and undesirable free-oil by-product is decreased by the inclusion of the amine oxide catalyst.

13 Claims, No Drawings

USE OF AMINE OXIDE IN THE H₂O₂ OXIDATION OF ALIPHATIC MERCAPTAN TO SULFONIC ACID

BACKGROUND OF THE INVENTION

Hydrocarbyl sulfonate salts are very effective surfactants and can be used for example in dishwashing detergent or laundry detergents. The $C_{10-20}$ aliphatic sulfonates in which the sulfonate group is on an internal carbon atom are particularly effective. Such compositions can be made by oxidizing an internal mercaptan with an oxidizing agent such as nitric acid, oxygen, hydrogen peroxide and the like. One problem with these processes is that the oxidation can produce a substantial portion of byproducts that are insoluble in aqueous base and soluble in aliphatic hydrocarbons such as pentane. These by-products are referred to as "free-oil" and include hydrocarbyl disulfides, thioesters and the like. This represents a substantial waste of starting materials and also complicates the process by requiring purification to remove the large amount of free-oil. Thus, a need exists for a process capable of oxidizing hydrocarbyl mercaptans to the corresponding sulfonic acid or salt in high yield and with minimal coproduction of free-oil.

SUMMARY OF THE INVENTION

It has now been discovered that hydrocarbyl mercaptans can be oxidized to the corresponding sulfonate salt in high yield with reduced coproduction of free-oil by reacting the hydrocarbyl mercaptan with aqueous hydrogen peroxide in the presence of a base and an amine oxide catalyst.

DESCRIPTION OF THE PREFERRED EMBODIMENTS

A preferred embodiment of the invention is a process for oxidizing a hydrocarbyl mercaptan to the corresponding sulfonic acid salt, said process comprising reacting said hydrocarbyl mercaptan with aqueous hydrogen peroxide in the presence of a base and a tert-amine oxide catalyst, said process being characterized by having high selectivity to sulfonic acid salt and reduced free-oil by-product.

Hydrocarbyl mercaptans that may be oxidized to sulfonic acids or salts according to the present invention include aliphatic, cycloaliphatic and aromatic mercaptans. Representative examples are 2-mercapto butane, 1-mercapto decane, 1-mercapto-2-ethylhexane, 7-mercapto-tetradecane, cyclohexyl mercaptan, cycloheptyl mercaptan, cyclooctyl mercaptan, cyclododecyl mercaptan, phenyl mercaptan, 2-mercapto toluene, 1-mercapto naphthalene, 4-mercapto-1,1'-biphenyl and the like.

The most preferred hydrocarbyl mercaptans are the aliphatic hydrocarbyl mercaptans such as butyl mercaptan, isobutyl mercaptan, 2-ethylhexyl mercaptan, 2-mercapto dodecane, 4-mercapto dodecane, 6-mercapto dodecane, 1-mercapto tetradecane, 6-mercapto tetradecane, 7-mercapto hexadecane, 1-mercapto octadecane, 1-mercapto eicosane, 10-mercapto eicosane, and the like.

Still more preferably the aliphatic hydrocarbyl mercaptan contains about 10-20 carbon atoms and the mercaptan substituent is bonded to an internal carbon atom or mainly to internal carbon atoms. Most preferably the internal aliphatic hydrocarbyl mercaptans is mainly secondary mercaptans with none or only minor amounts (e.g. less than 10 mole percent) tertiary mercaptans.

In a highly preferred mode of operation the internal aliphatic hydrocarbyl mercaptan is obtained by isomerizing an alpha-olefin or mixture of alpha-olefins containing about 10-20 carbon atoms to obtain a mixture of internal olefins and then reacting the internal olefin mixture with hydrogen sulfide in the presence of an acidic catalyst (e.g. $BF_3$) to obtain mainly internal secondary alkyl mercaptans. Such mixtures are mainly (e.g. 80-95 mole percent) sec-mercaptans and contain only minor amounts, up to about 20 mole percent, of tert-mercaptans.

The reaction is catalyzed by an amine oxide. These are tert-amine N-oxides. Of these the more preferred are the trialkylamine oxides. Representative examples are
triethylamine oxide,
tri-n-butylamine oxide,
hexyl dimethylamine oxide,
octyl dimethylamine oxide,
dihexyl methylamine oxide,
decyl dimethylamine oxide,
decyl diethylamine oxide,
decyl methyl ethylamine oxide,
tridecylamine oxide,
dodecyl dimethylamine oxide, and the like.

The more preferred amine oxides are the $C_{6-20}$ alkyl dimethylamine oxides such as
hexyl dimethylamine oxide,
heptyl dimethylamine oxide,
octyl dimethylamine oxide,
nonyl dimethylamine oxide,
decyl dimethylamine oxide,
dodecyl dimethylamine oxide,
tetradecyl dimethylamine oxide,
hexadecyl dimethylamine oxide,
octadecyl dimethylamine oxide,
eicosyl dimethylamine oxide, and the like.

The amount of amine oxide is a catalytic amount. This means an amount which will modify the course of the reaction to yield a product which contains less free-oil compared to that produced in the absence of the catalytic amount. A useful range in which to operate is about 0.2-20 parts by weight amine oxide per 100 parts of hydrocarbyl mercaptan. A more preferred range is about 0.5-10 parts by weight and most preferably about 1-3 parts by weight per 100 parts of hydrocarbyl mercaptan.

The reaction is conducted in the presence of a basic compound. Examples of basic compounds are sodium hydroxide, potassium hydroxide, calcium hydroxide, magnesium hydroxide, calcium oxide, sodium methoxide, sodium isopropoxide, potassium methoxide, potassium isopropoxide, sodium tert-butoxide and the like. The more preferred bases are the alkali metal hydroxides and most preferably sodium hydroxide.

The amount of base is preferably an amount sufficient to convert the sulfonic acid produced to a sulfonate salt. This means there should be at least one equivalent of base per equivalent of mercaptan. With mono-mercaptans and alkali metal hydroxides this results in at least one mole part of alkali metal hydroxide per mole part of mercaptan. There is no real upper limit on the amount of base but for practical reason the amount is generally kept under about 5 equivalents of base per equivalent of mercaptan.

The base is preferably in the form of a solution or slurry in water. In this system the alkoxides will of course be hydrolyzed to hydroxides. The amount of water can vary over a wide range. A useful range is about 100–1,000 parts of water per 100 parts of base by weight.

The preferred mode of operation is to form a mixture of the hydrocarbyl mercaptan, the amine oxide and the aqueous base and while stirring at reaction temperature, slowly adding aqueous hydrogen peroxide. Based upon economics and ease of operation, a preferred temperature range is about 20° C. up to reflex (approximately 100° C.).

The aqueous hydrogen peroxide may be in any concentration although a preferred concentration range is about 10–50 weight percent $H_2O_2$ and more preferably about 30 weight percent $H_2O_2$. The amount of aqueous hydrogen peroxide should be an amount sufficient to oxidize all or most of the mercaptan groups to sulfonic acid groups. This stoichiometry requires about three moles of hydrogen peroxide per equivalent of mercaptan. A useful range in which to operate is about 100–110% of the stoichiometric amount of hydrogen peroxide. With this and all reactions involving the use of concentrated hydrogen peroxide, care should be taken to avoid the accumulation of unreacted peroxide. And unreacted hydrogen peroxide remaining after the reaction can be decomposed by adding aqueous sodium sulfite or some other mild reducing agent.

The time required to feed the aqeous hydrogen peroxide will depend upon scale and reaction temperature. The addition rate should be controlled to avoid buildup of an excessive amount of unreacted $H_2O_2$ in the reaction mixture. It is not known just what is an excessive amount but as a guide, the rate should be such as to maintain the $H_2O_2$ concentration in the aqueous reaction phase below about 10 weight percent and more preferably below about 5 weight percent. A reaction feed time of about 1–8 hours at 50°–70° C. will accomplish this.

After completion of the hydrogen peroxide feed, any unreacted $H_2O_2$ in the reaction mixture can be removed by adding an equivalent amount of sodium sulfite. The product in the form of a sulfonate salt can then be recovered by conventional means such as by desalting and subsequent separation from isopropanol phase.

The following examples serve to illustrate the best mode now known for conducting the process and also the comparative results obtained without the amine oxide catalyst.

EXAMPLE 1

In a reaction vessel was placed 40 grams of a mixture of mainly secondary straight chain $C_{16}$ aliphatic mercaptans, 1.33 grams of a 30 weight percent aqueous solution of tetradecyl dirmethylamine oxide and 18.03 grams of a 10N aqueous sodium hydroxide solution. This mixture was stirred and 60 ml of 30 weight percent aqueous hydrogen peroxide was added dropwise at 22°–78° C. over a 3.5 hours period. Some foaming was encountered towards the end of the reaction. The product contained two liquid phases and some white solids. A KI test for $H_2O_2$ was negative but a small amount of sodium sulfite was added. Then 200 ml of isopropanol and 100 ml of water were added. Then sodium carbonate powder was added to saturate the aqueous phase causing phase separation. The aqueous phase was separated and discarded. The alcohol was filtered to remove a small amount of solids and then concentrated under vacuum. Then 400 ml of a 50/50 alcohol (95% ethanol/5% methanol)-water mixture was added to the concentrate which was then extracted twice with pentane to remove free-oil. The pentane was evaporated leaving 1.5 grams of oil which represented 3 weight percent of the total product. The balances of the product was sodium tetradecyl sulfonate. The sodium tetradecyl sulfonates in the concentrate can be recovered by removing the water and alcohol under vacuum.

EXAMPLE 2

This is a comparative example showing the results without the amine oxide catalyst.

The reaction vessel was charged with 40 grams of the same tetradecyl mercaptan used in Example 1 and 18 grams of 10N aqueous sodium hydroxide. While stirring 60 ml of 30 weight percent hydrogen peroxide was added dropwise over a 6 hour 15 minute period at 22°–80° C. (one brief excursion to 107° C.). The reaction mixture was worked up in the same manner as in Example 1. The amount of pentane soluble free-oil was 10.1 grams or 19.8 weight percent of the total product.

The results clearly show that the use of the amine oxide catalyst decreased the amount of free-oil by-product from 19.8 weight percent down to only 3 weight percent, an 84.8 percent

We claim:

1. A process for oxidizing a hydrocarbyl mercaptan to the corresponding sulfonic acid salt, said process comprising reacting said hydrocarbyl mercaptan with aqueous hydrogen peroxide in the presence of a base and a tert-amine oxide catalyst, said process being characterized by having high selectivity to sulfonic acid salt and reduced free-oil by-product.

2. A process of claim 1 wherein said hydrocarbyl mercaptan is an aliphatic hydrocarbyl mercaptan.

3. A process of claim 2 wherein said aliphatic hydrocarbyl mercaptan contains about 10–20 carbon atoms.

4. A process of claim 3 wherein said aliphatic hydrocarbyl mercaptan comprises a mixture of predominantly secondary mercaptans containing up to about 20 weight percent tertmercaptans.

5. A process of claim 1 wherein said amine oxide is a trialkylamine oxide.

6. A process of claim 5 wherein said trialkylamine oxide is a $C_{6-20}$ alkyl dimethylamine oxide.

7. A process of claim 1 wherein said base is an alkali metal hydroxide.

8. A process of claim 7 wherein said alkali metal hydroxide is sodium hydroxide.

9. A process for making a $C_{12-18}$ mainly secondary aliphatic sodium sulfonate, said process comprising reacting about 1 mole part of a mixture of mainly secondary $C_{12-18}$ aliphatic mercaptans with at least a stoichiometric amount of aqueous hydrogen peroxide in the presence of at least 1 mole part of aqueous sodium hydroxide and a catalytic amount of a trialkylamine oxide.

10. A process of claim 9 wherein said trialkylamine oxide is a $C_{6-20}$ alkyl dimethylamine oxide.

11. A process of claim 9 conducted at a temperature within the range of about 20°–100° C.

12. A process of claim 11 wherein said trialkylamine oxide is tetradecyldimethylamine oxide.

13. A process of claim 11 wherein said aqueous hydrogen peroxide is about 30 weight percent hydrogen peroxide.

* * * * *